United States Patent
Chechik (10) Patent No.: US 8,939,889 B1
(45) Date of Patent: Jan. 27, 2015

(54) PUMP BULB FOR AN IMPLANTABLE PENILE PROSTHETIC

(71) Applicant: Coloplast A/S, Humlebaek (DK)

(72) Inventor: Joel Chechik, Minneapolis, MN (US)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 13/972,932

(22) Filed: Aug. 22, 2013

(51) Int. Cl.
*A61F 5/00* (2006.01)
*A61F 2/26* (2006.01)

(52) U.S. Cl.
CPC ..................................... *A61F 2/26* (2013.01)
USPC ............................................................ 600/40

(58) Field of Classification Search
CPC ......... A61F 2/26; B05B 11/061; F04B 33/00; F04B 43/08; F04B 45/00; F04B 45/06; A61H 2201/5056; A61H 9/0078
USPC ..................... 600/38–41; 222/206, 209, 213; 417/435, 437, 472, 557, 572
See application file for complete search history.

(56) References Cited

U.S. PATENT DOCUMENTS

| | | | |
|---|---|---|---|
| D233,898 S | 12/1974 | Warren | |
| 4,050,311 A * | 9/1977 | Leach | ........................... 600/498 |
| 4,407,278 A | 10/1983 | Burton et al. | |
| 4,881,530 A | 11/1989 | Trick | |
| D314,018 S | 1/1991 | Rosenthal | |
| 5,062,417 A | 11/1991 | Cowen | |
| 5,167,611 A | 12/1992 | Cowan | |
| 5,250,020 A | 10/1993 | Bley | |
| 5,263,981 A | 11/1993 | Polyak et al. | |
| 5,344,388 A * | 9/1994 | Maxwell et al. | ................. 600/40 |
| 5,556,258 A * | 9/1996 | Lange et al. | ..................... 417/63 |
| 5,704,895 A | 1/1998 | Scott et al. | |
| D412,537 S | 8/1999 | Underwood | |
| D414,219 S | 9/1999 | Karls | |
| 6,015,380 A | 1/2000 | Subrini | |
| 7,914,439 B2 | 3/2011 | Kuyava et al. | |
| 7,946,975 B2 | 5/2011 | George et al. | |
| 8,167,788 B2 | 5/2012 | Fogarty et al. | |
| 8,337,392 B2 | 12/2012 | Morningstar | |

(Continued)

FOREIGN PATENT DOCUMENTS

| | | |
|---|---|---|
| EP | 0065853 A1 | 12/1982 |
| EP | 0714300 A1 | 6/1996 |

(Continued)

OTHER PUBLICATIONS

AMS 700 Series Penile Prosthesis Users Guide 2001.
Extended Search Report of Nov. 5, 2013 from EPO.

*Primary Examiner* — Samuel Gilbert
(74) *Attorney, Agent, or Firm* — Coloplast Corp., Coloplast A/S; Nick Baumann (57) ABSTRACT

A penile prosthetic includes an inflatable member that is implantable into a penis of a user, a reservoir that is implantable in an abdomen, and a pump. The pump is configured to be attached between the inflatable member and the reservoir and is implantable in a scrotum. The pump includes a pump bulb having an internal cavity formed by a side surface connected between a bottom surface and a top surface of the pump bulb. The side surface provides an outside circumference of the pump bulb and includes at least two concave side walls with each concave side wall connected between two adjacent convex lobes of the pump bulb.

13 Claims, 8 Drawing Sheets

(56) References Cited

U.S. PATENT DOCUMENTS

| | | |
|---|---|---|
| 8,617,050 B2 | 12/2013 | Morningstar |
| 8,641,601 B2 | 2/2014 | Ellering |
| 2004/0138523 A1 | 7/2004 | Kuyava et al. |

FOREIGN PATENT DOCUMENTS

| | | |
|---|---|---|
| EP | 1220666 A2 | 7/2002 |
| WO | 9505172 A1 | 2/1995 |
| WO | 0059491 A2 | 10/2000 |

* cited by examiner

PUMP BULB FOR AN IMPLANTABLE PENILE PROSTHETIC

BACKGROUND

An implanted penile prosthetic is effective in relieving erectile dysfunction in men.

A penile prosthetic typically includes an inflatable cylinder that is implanted in each corpora cavernosum of the penis, a reservoir implanted in the abdomen that communicates with the cylinders, and a pump, often located in the scrotum, that is employed to move liquid from the reservoir into the cylinders for inflation of the implanted cylinders.

In a typical application, the user squeezes a bulb of the pump multiple times to draw liquid out of the reservoir and pump the liquid into the cylinders. The repeated squeezing of the bulb thus moves the liquid from the reservoir into the cylinders to provide the user with an erect penis. The user may return the penis to its flaccid state by selectively transferring the liquid from the cylinders back into the reservoir.

Some users suffer from a reduced range of motion in their fingers or from reduced dexterity, at times due to arthritis of the hand. These users can have difficulty in grasping the pump bulb or in repeatedly squeezing the pump bulb.

Penile prostheses have proven effective in relieving erectile dysfunction in men. However, users and their surgeons would welcome improvements to penile prostheses.

SUMMARY

One aspect provides an implantable penile prosthetic including a pump bulb having a lobed structure that is easier to grasp for users with reduced dexterity and walls that make squeezing of the pump bulb more efficient compared to spherical pump bulbs. The walls are sized to receive a finger or a thumb of the user and the lobes are sized to reduce or eliminate the tendency of the pump bulb from slipping out of the grasp of the user. Some users suffer from a reduced range of motion in their fingers or from reduced dexterity (perhaps due to arthritis of the hand), and the lobes and walls of the pump bulb allow these users to more effectively locate, grasp, and squeeze the pump bulb.

One aspect provides an implantable penile prosthetic including an inflatable member that is implantable into a penis of a user, a reservoir that is implantable in an abdomen, and a pump. The reservoir is configured to contain liquid useful in inflating the inflatable member. The pump is configured to be attached between the inflatable member and the reservoir and be implanted in a scrotum. The pump includes a pump bulb having an internal cavity formed by a side surface connected between a bottom surface of the pump bulb and a top surface of the pump bulb that includes a conduit that is configured to communicate with one of the inflatable member and the reservoir. The side surface provides an outside circumference of the pump bulb and includes at least two concave side walls connected between two adjacent convex lobes of the pump bulb. A first distance between the two concave side walls is less than a second distance between the two adjacent convex lobes.

One aspect provides an implantable penile prosthetic including a pump attachable with tubing between an inflatable member that is implantable into a penis and a reservoir that is implantable in an abdomen. The reservoir is configured to contain liquid useful in inflating the inflatable member. The pump includes a pump bulb having an internal cavity formed by a side surface connected between a top surface and a bottom surface of the pump bulb such that the side surface forms an outer circumference of the pump bulb. The pump bulb includes three lobes. Each lobe is convex in shape when viewed in a lateral cross-section taken parallel between the top surface and the bottom surface. Each lobe is spaced apart from an adjacent lobe by a spacing that provides a finger-width access recess to the pump bulb. The side surface of the pump bulb includes three side walls, with each side wall connected between two of the three lobes with each side wall concave when viewed in the lateral cross-section taken parallel between the top surface and the bottom surface.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

The term "proximal" as employed in this application means that the referenced part is situated next to or near the point of attachment or origin or a central point: as located toward a center of the human body. The term "distal" as employed in this application means that the referenced part is situated away from the point of attachment or origin or the central point: as located away from the center of the human body. A distal end is the furthest endmost location of a distal portion of a thing being described, whereas a proximal end is the nearest endmost location of a proximal portion of the thing being described. For example, the glans penis is located distal, and of the crus of the penis is located proximal relative to the male body such that a distal end of a corpora cavernosum of the patient extends about midway into the glans penis.

Embodiments provide a pump for an implantable penile prosthetic that is provided with a pump bulb that is easier to grasp and easier to pump, particularly for those users who suffer from arthritis or limited dexterity of the hand. Embodiments provide a pump having a pump bulb including multiple lobes, with a finger access area provided between two adjacent lobes to configure the pump bulb to more naturally fit in the hand between the fingers of the user. One example of the pump bulb includes three lobes and is referred to as a Tri-Flate pump bulb.

In contrast, some implantable penile prosthetics are provided with a spherical pump bulb that operates to pump liquid from the prosthetic reservoir to the penile implants. However, some users have experienced sliding and movement of the spherical pump bulb within the tissue of the scrotum that presents challenges in grasping and/or repeatedly pumping the spherical pump bulb. The pump bulb described below includes multiple lobes providing multiple finger access areas that provide an improved grasping surface with an easier to manipulate pump, particularly for users with limited dexterity.

Figure 1:
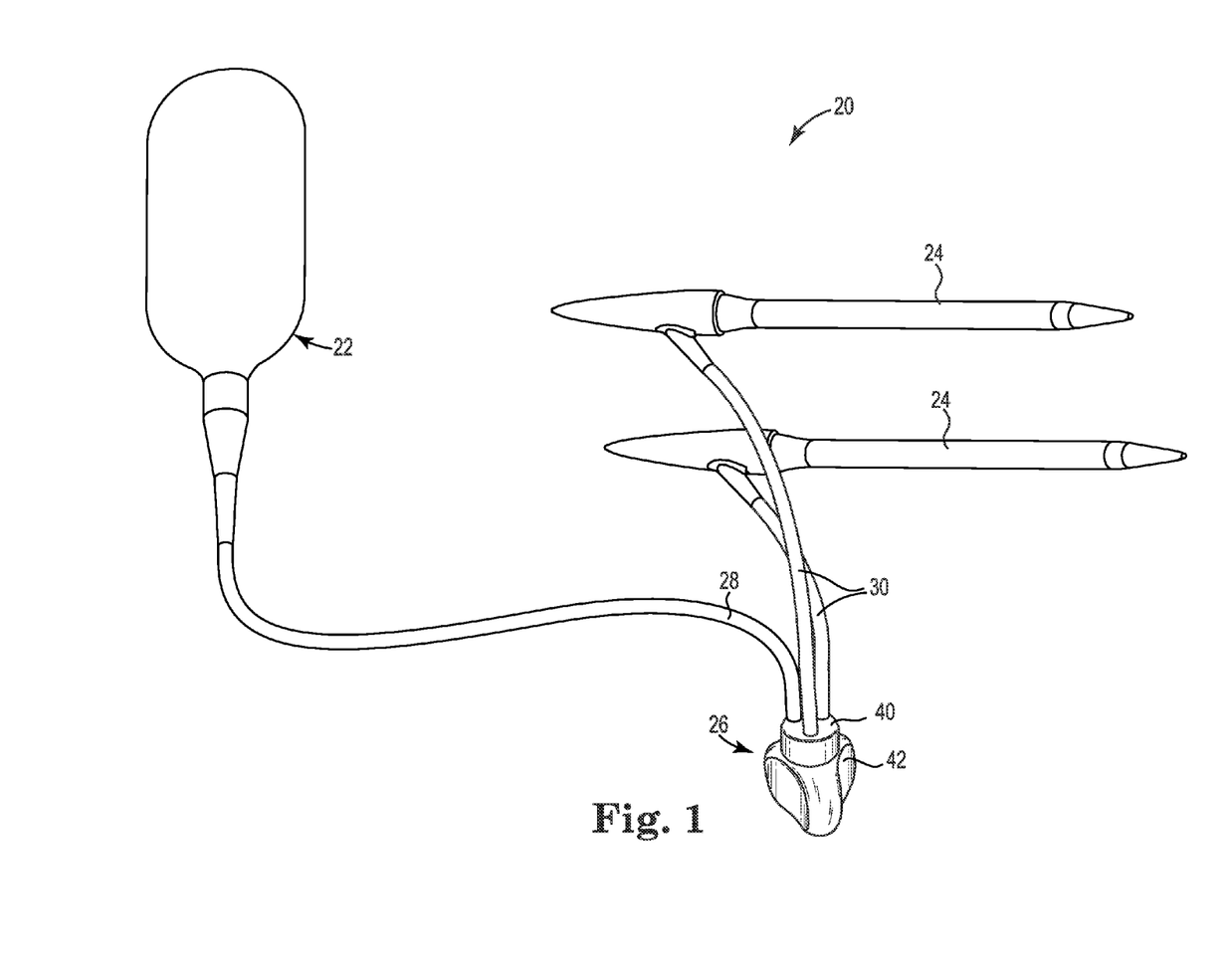
FIG. 1 is a perspective view of one embodiment of an implantable penile prosthetic including a pump attached to inflatable penile inserts and a reservoir.

FIG. 1 is a perspective view of one embodiment of an implantable penile prosthetic 20. The penile prosthetic 20 includes a reservoir 22 communicating with inflatable members 24 across a pump 26. The reservoir 22 is connected with the pump 26 by tubing 28, and inflatable members 24 are connected with the pump 26 by tubing 30.

The components (reservoir 22, implants 24, pump 26, and tubing 28, 30) of the penile prosthetic 20 are generally provided unassembled in a kit of parts. The components are assembled immediately prior to surgery, or intra-operatively, as determined by the surgeon. For example, each of the tubing lengths 28, 30 have a portion that is attached to the reservoir 22 and a portion that is attached to the inflatable members 24, respectively, and a portion that is secured to a housing 40 that extends from a pump bulb 42 of the pump 26. The tubing lengths are attached by some form of tubing connector useful with surgical implants. The components of the penile prosthetic 20 are illustrated in an assembled configuration in FIG. 1 for descriptive clarity.

The reservoir 22 is sized for implantation within the human body, for example within the abdomen. The reservoir 22 is configured to retain a volume of liquid useful in inflating the inflatable members, for example with a volume in a range of 50-350 cc. Suitable materials for fabricating the reservoir 22 include silicone, polymers such as urethanes, a blend of polymers with urethane, copolymers of urethane, or the like. In one exemplary fabrication process, one of the suitable materials identified above is molded into a container shape appropriate for implantation in the space of Retzius or in the abdomen.

The inflatable members 24 are provided as a pair of inflatable cylinders, each of which is sized to be implanted into a corpora cavernosum of the penis. Each of the cylinders a rear tip that is implanted toward the crus of the penis and a distal end that is implanted within the glans penis. The cylinders are fabricated from material configured to collapse and be flexible when the cylinders are deflated to provide the penis with a flaccid state and expand when the cylinders are inflated with liquid to provide the penis with an erect state. Suitable material for fabricating the cylinders 32 includes silicone, polymers such as urethanes, a blend of polymers with urethane, copolymers of urethane, or the like. Suitable cylinders are available from Coloplast Corp., Minneapolis, Minn.

Figure 2:
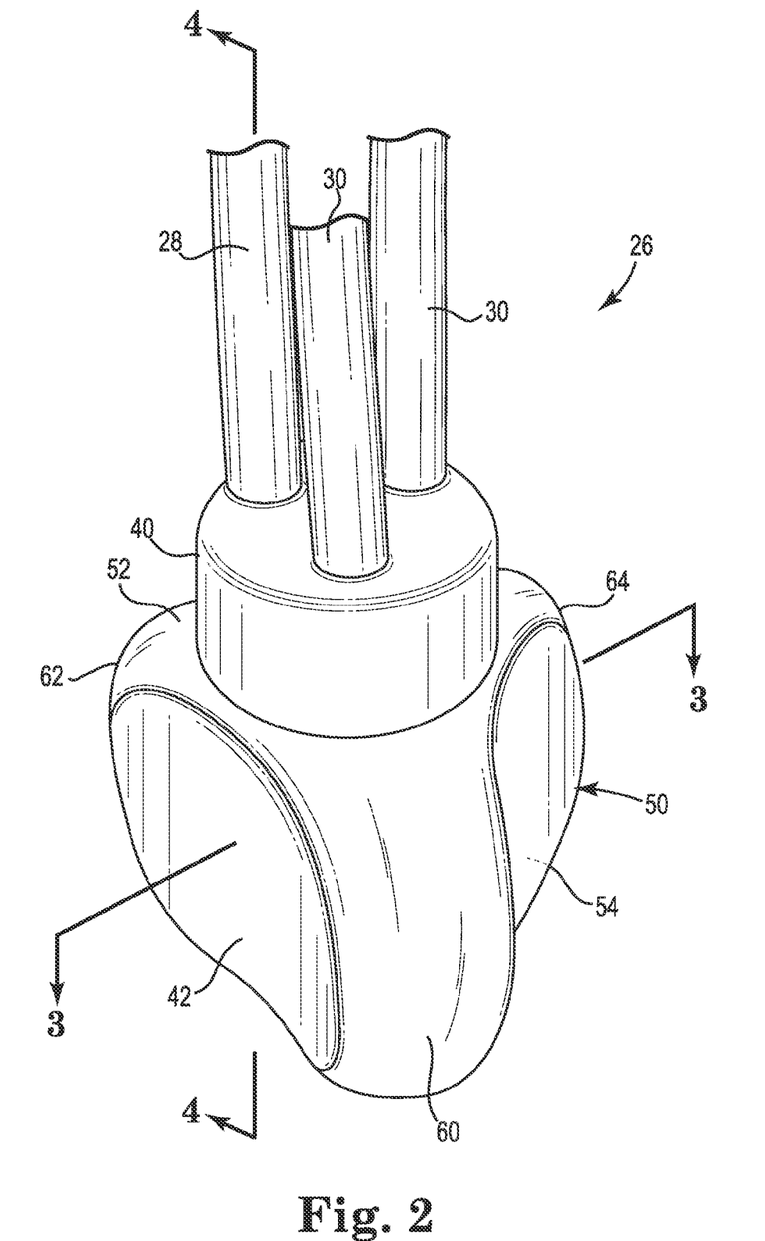
FIG. 2 is a perspective view of one embodiment of the pump illustrated in FIG. 1.

FIG. 2 is a perspective view of the pump 26.

The housing 40 is attached to the pump bulb 42 and includes valve assemblies (described below) in communication with conduits that extend from the housing 40 for attachment with the tubing 28, 30.

The pump bulb 42 is formed by a side surface 50 that is connected between a top surface 52 and a bottom surface 54. The top surface 52 of the pump bulb 42 includes the conduits 28, 30 that are configured to be attached with and communicate with one of the inflatable member 24 or the reservoir 22. The side surface 50 forms an outer circumference of the pump bulb 26. The side surface 50 is not uniformly convex, as would be the case if the pump bulb were spherical. The side surface 50 is a compound surface having regions of concavity connected with regions of convexity. The pump bulb 26 includes a first lobe 60, a second lobe 62, and a third lobe 64 as illustrated in FIG. 2, where each lobe is spaced apart from an adjacent lobe to provide a finger-width access recess that improves a user's ability to grasp and pump the pump bulb 42.

Figure 3:
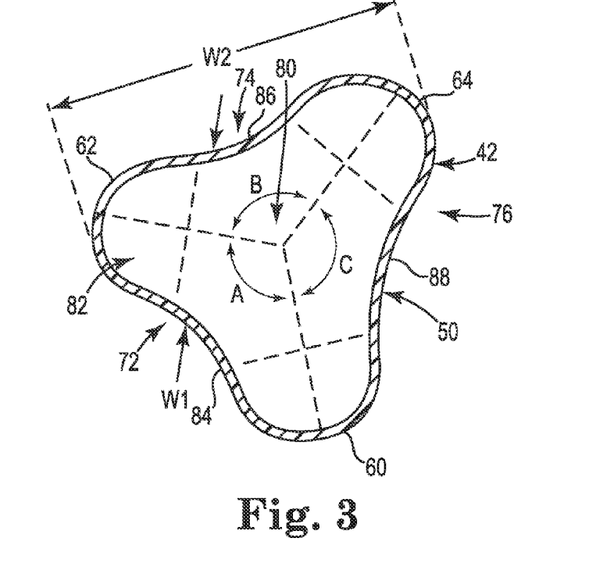
FIG. 3 is a lateral cross-sectional view taken parallel between a top surface and a bottom surface of a bulb of the pump illustrated in FIG. 2.

FIG. 3 is a lateral cross-sectional view of the pump bulb 42 taken parallel between the top surface 52 and the bottom surface 54 (FIG. 2) of the pump bulb 42. Each of the lobes 60, 62, 64 is convex in shape when viewed in the lateral cross-section of FIG. 3. Regarding the convex lobes, the first lobe 60 is spaced apart from the second lobe 62 by a spacing 70, the second lobe 62 is spaced apart from a third lobe 64 by a spacing 72, and the third lobe 64 is spaced apart from the first lobe 60 by a spacing 74.

In one embodiment, each of the three lobes 60, 62, 64 is symmetrically spaced by equal spacings with each lobe oriented 120 degrees from an adjacent lobe. In one embodiment, each lobe is spaced apart from an adjacent lobe by a spacing of about 0.25 inches to provide a gripping area for the fingers of the user. In one embodiment, each lobe is spaced apart from an adjacent lobe by a spacing in a range from 0.12 inches to 1 inches to provide a gripping area for the fingers of the user.

In one embodiment, the lobes 60, 62, 64 are not symmetrically spaced and the first lobe 60 is oriented relative to the second lobe 62 by the angle A, the second lobe 62 is oriented relative to the third lobe 64 by the angle B, and the third lobe 64 is oriented relative to the first lobe 60 by the angle C, where the angle A is different from at least one of the angles B, and C. One of the angles A, B, C can be different from the other two angles, or all of the angles A, B, C can be different one from the other.

The pump bulb 42 is provided with an internal cavity formed by the side surface 50 and the top and bottom surfaces 52, 54. The internal cavity includes a central cavity 80 and three lobe cavities 82. The central cavity 80 is larger than any one lobe cavity 82 and the central cavity 80 retains a majority of the volume of liquid that is ejected by the pump bulb 42. During use, the user's fingers are directed to the spacings 72, 74, 76, which are appropriately located for applying pressure and multiple directions to the central cavity 80.

The side surface 50 includes three side walls 84, 86, 88. The sidewall 84 is connected between the first lobe 60 and the second lobe 62. The sidewall 86 is connected between the second lobe 62 and the third lobe 64. The third sidewall 88 is connected between the third lobe 64 and the first lobe 60. Each side wall 84, 86, 88 is concave when viewed in the lateral cross-section that is taken between the top surface 52 and the bottom surface 54 of the pump bulb 42 as illustrated in FIG. 3. The side surface 50 is a compound surface having regions of concavity connected with regions of convexity, with each side wall being concave in at least one direction and each lobe being convex.

The concave side walls 84, 86, 88 are each sized to receive a thumb or a finger of the user. The convex lobes 60, 62, 64 are each configured to reduce sliding of the pump bulb 42 through fingers of the user during pumping. Specifically, a first external width W1 between the two concave side walls 84, 84 (as an example) is less than a second external width W2 of the adjacent convex lobes 60, 62 or 62, 64. The width of any two side walls is less than the width of any two lobes. Each of the lobes 60, 62, 64 is sized and configured to provide a wide obstacle that resists slipping through the user's fingers as the user squeezes the concave sides 84, 86, 88 of the bulb 42. In this manner, the bulb 42 is easier to use for those who suffer from arthritis and limited dexterity. Squeezing of the walls 84, 86, 88 delivers an increased and more effective evacuation force to the central cavity 80 as compared to spherical pump bulbs, and this makes squeezing of the pump bulb 42 more efficient in delivering liquid to the inflatable members.

Figure 4:
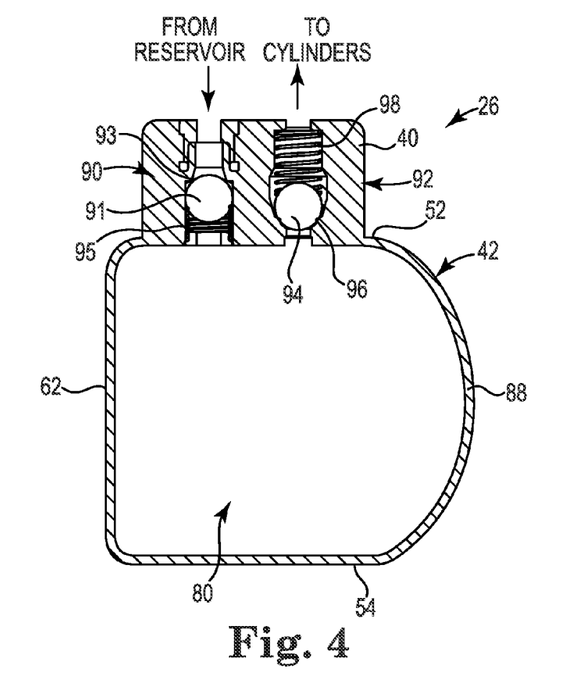
FIG. 4 is a longitudinal cross-sectional view of the bulb of the pump taken vertically from the top surface through the bottom surface between two adjacent lobes.

FIG. 4 is a longitudinal cross-sectional view of the pump 26. The longitudinal cross-section is taken vertically from the top surface 52 through the bottom surface 54 between the third lobe 64 and the first lobe 60 (FIG. 2 and FIG. 3). In one embodiment, each side wall 84, 86, 88 between each adjacent lobe is substantially planar when viewed in the longitudinal cross-section as illustrated in FIG. 4. Each lobe, including the lobe 62, is convex in shape when viewed in the longitudinal cross-section of FIG. 4 such that lobe 62 projects outward relative the central cavity 80.

The central cavity 80 of the pump bulb 42 communicates with the reservoir 22 and the cylinders 24 (FIG. 1) by two valve assemblies 90, 92. The valve assemblies are retained within the housing 40 and include an inlet valve assembly 90 and an exhaust valve assembly 92. The inlet valve assembly 90 includes a valve 91 that is biased against a valve seat 93 by a spring 95. The exhaust valve assembly 92 includes a valve 94 that is biased against a valve seat 96 by a spring 98.

The pump 26 functions to inflate the cylinders 24 in the following manner. After the pump bulb 42 is squeezed a lower pressure (or suction) is formed in the central cavity 80 and liquid is drawn from the reservoir across the inlet valve 90 and into the central cavity 80. Subsequent squeezing of the pump bulb 42 ejects the liquid that is in the central cavity 80 across the exhaust valve 92 and into the cylinders 24. As described above and with reference to FIG. 3, the spacings 72, 74, 76 between the lobes 60, 62, 64, respectively, allow the user to fully collapse the bulb 42 and thus provide a pump bulb 42 that is easier to squeeze multiple times, particularly for those with limited dexterity in their hands.

Suitable materials for fabricating the pump 26 include silicone, polymers such as urethanes, a blend of polymers with urethane, copolymers of urethane, or the like. In one exemplary fabrication process, one of the suitable materials identified above is molded into the shape of the pump bulb illustrated in one of FIG. 2, 6, 9, or 10.

Figure 5:
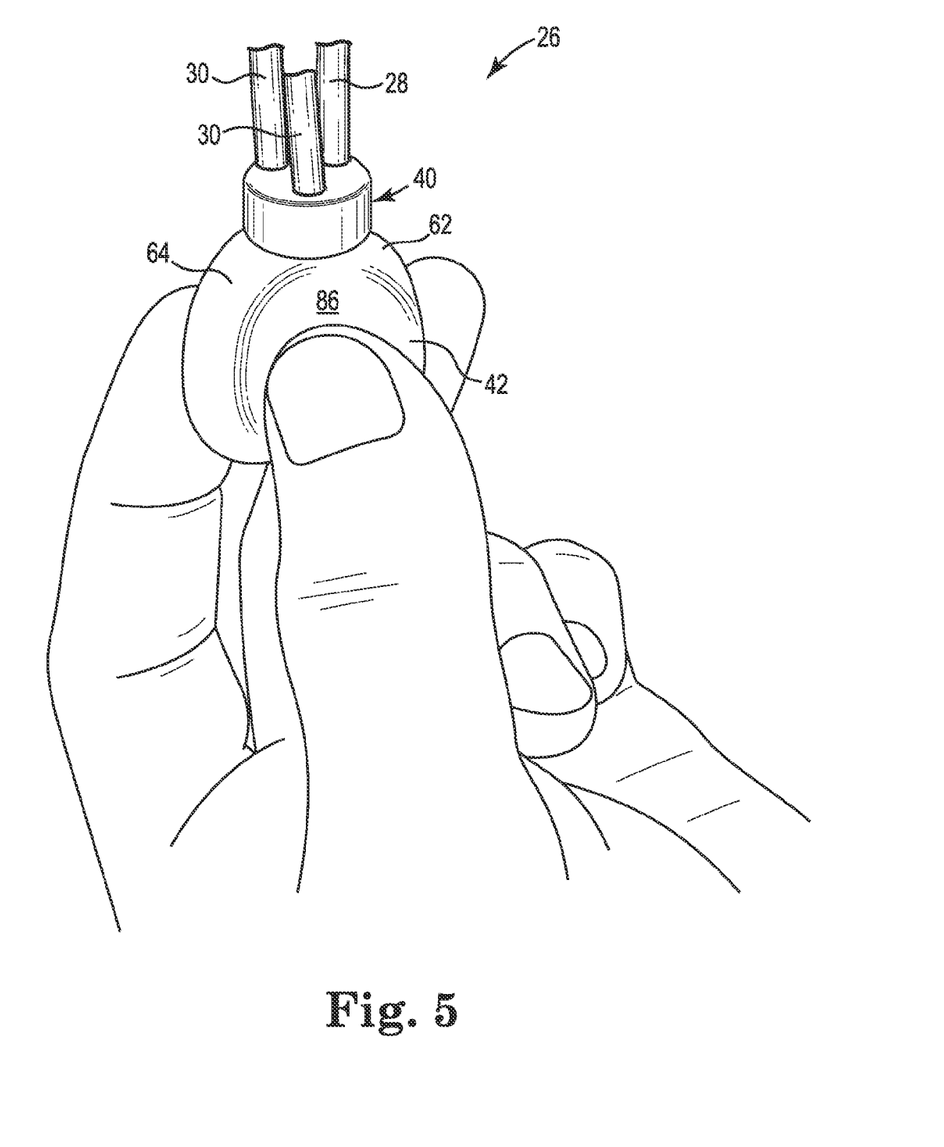
FIG. 5 is a perspective view of a hand accessing finger access areas between lobes of the bulb of the pump illustrated in FIG. 2.

FIG. 5 is a schematic view of a hand grasping the pump 26. The pump 26 is sized to be implanted within the scrotum. However, the operation of the pump 26 and the improved grasping surfaces are best understood in isolation from the tissues of the body. The pump bulb 42 provides a concave wall surface 86 between two lobes 62, 64. The concave surface 86 is configured to receive the pad of the thumb, and two of the other concave surfaces (not shown) are sized to receive the pad of a finger. The lobes 62, 64 direct the fingers and the thumb to the appropriate concave wall and provide a structural exterior feature that is easy to locate. The multi-lobal shape reduces or eliminates the sliding of the pump bulb 42 between the fingers during squeezing of the pump bulb 42.

In one embodiment, the exterior surface of the pump 26 is smooth and the user is allowed to grasp the pump bulb 42 by virtue of the structural shape of the lobes 60, 62, 64 in conjunction with the side walls 84, 86, 88. In one embodiment, the exterior surface of the pump bulb 42 is fabricated to have increased wet sliding friction provided by a plurality of ribs, a sawtooth pattern, bumps, or other external surface feature added to the exterior surface.

Figure 6:
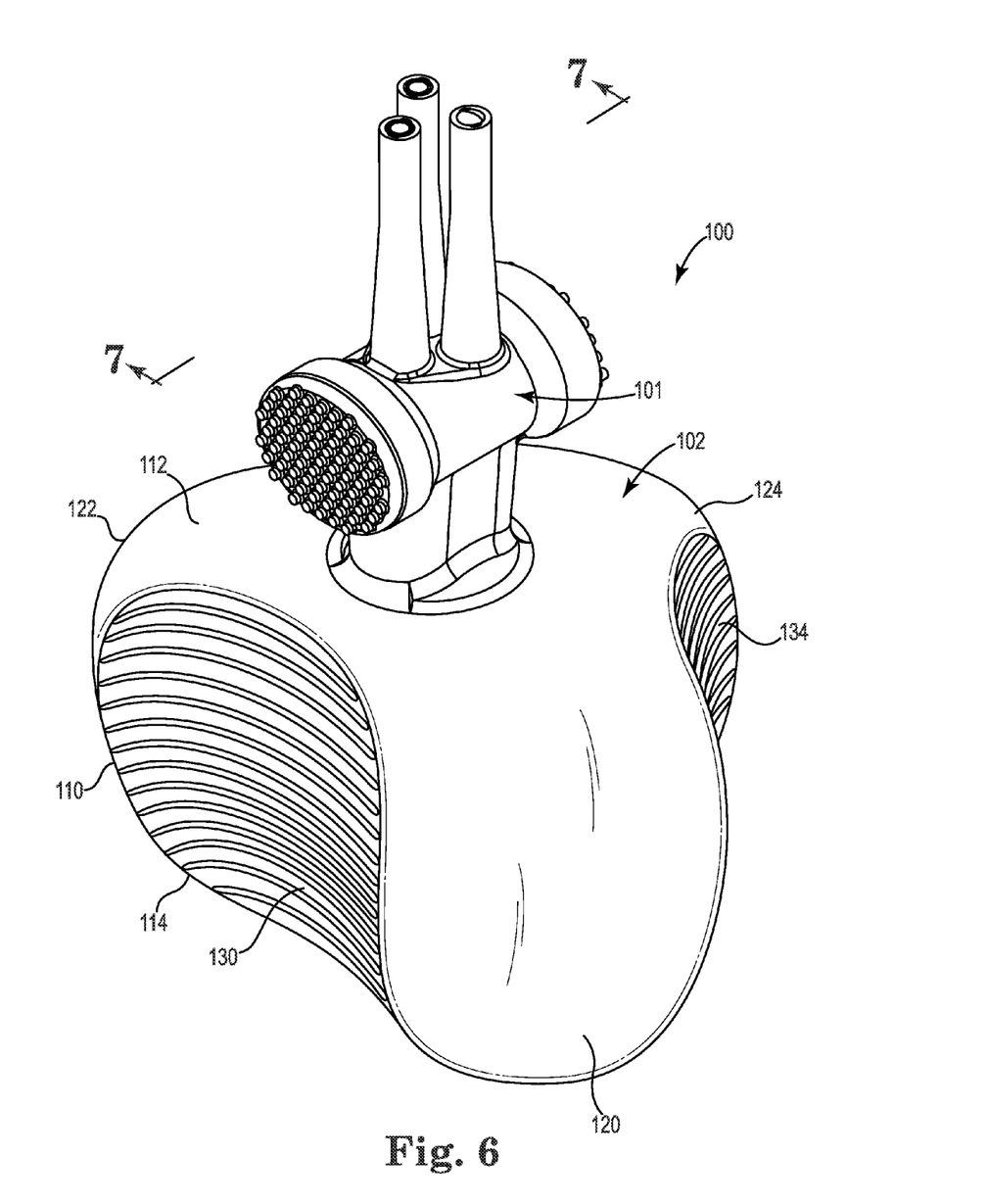
FIG. 6 is a perspective view of one embodiment of a pump suitable for use with an implantable penile prosthetic.

FIG. 6 is a perspective view of one embodiment of a pump 100 suitable for use with the penile prosthetic illustrated in FIG. 1. The pump 100 includes a stem 101 and a pump bulb 102. The stem 101 houses one or more valves that control the flow of liquid out of the pump bulb 102.

The pump bulb 102 is provided with walls between adjacent lobes, where each wall is concave in a lateral direction and concave in a longitudinal direction. The multi-concavity walls are connected to convex lobes. The walls 84, 86, 88 of the pump bulb 42 (FIG. 3) have one planar dimension; in contrast the walls of the pump bulb 102 have a concave shape in two of the cardinal directions, as described below.

The pump bulb 102 has an internal cavity that is formed by a side surface 110 connected between a top surface 112 and a bottom surface 114. The side surface 110 forms an outer circumference of the pump bulb 102. The pump bulb 102 includes three lobes 120, 122, 124. Each lobe is convex in shape when viewed in a lateral cross-section taken parallel between the top surface 112 and the bottom surface 114. Each lobe is convex in shape when viewed in a longitudinal cross-section taken from the top surface 112 to the bottom surface 114. Each lobe is spaced apart from an adjacent lobe by a spacing that provides access for a finger of the user.

The side surface 110 of the pump bulb 102 provides three side walls 130, 132 (not shown), and 134. Each side wall is connected between two of the three lobes. Each side wall 130, 132, 134 is concave (curved inwards) when viewed in the lateral cross-section taken parallel between the top surface and the bottom surface of the pump bulb. In addition, each side wall 130, 132, 134 is concave (curved inwards) when viewed in a longitudinal cross-section taken from the top surface 112 to the bottom surface 114 between two adjacent lobes (See FIG. 7). In this specification, the side walls 130, 132 are said to have multiple concavity.

The lobes 120, 122, 124 are configured to direct the fingers/thumb to a proper and comfortable squeezing position, and the concave walls 130, 132, 134 each provide a depression into which the user's finger will nestle. The combined geometry of the lobes and the walls makes the pump bulb 102 easy to locate, easy to grasp, and easy and efficient to pump.

Figure 7:
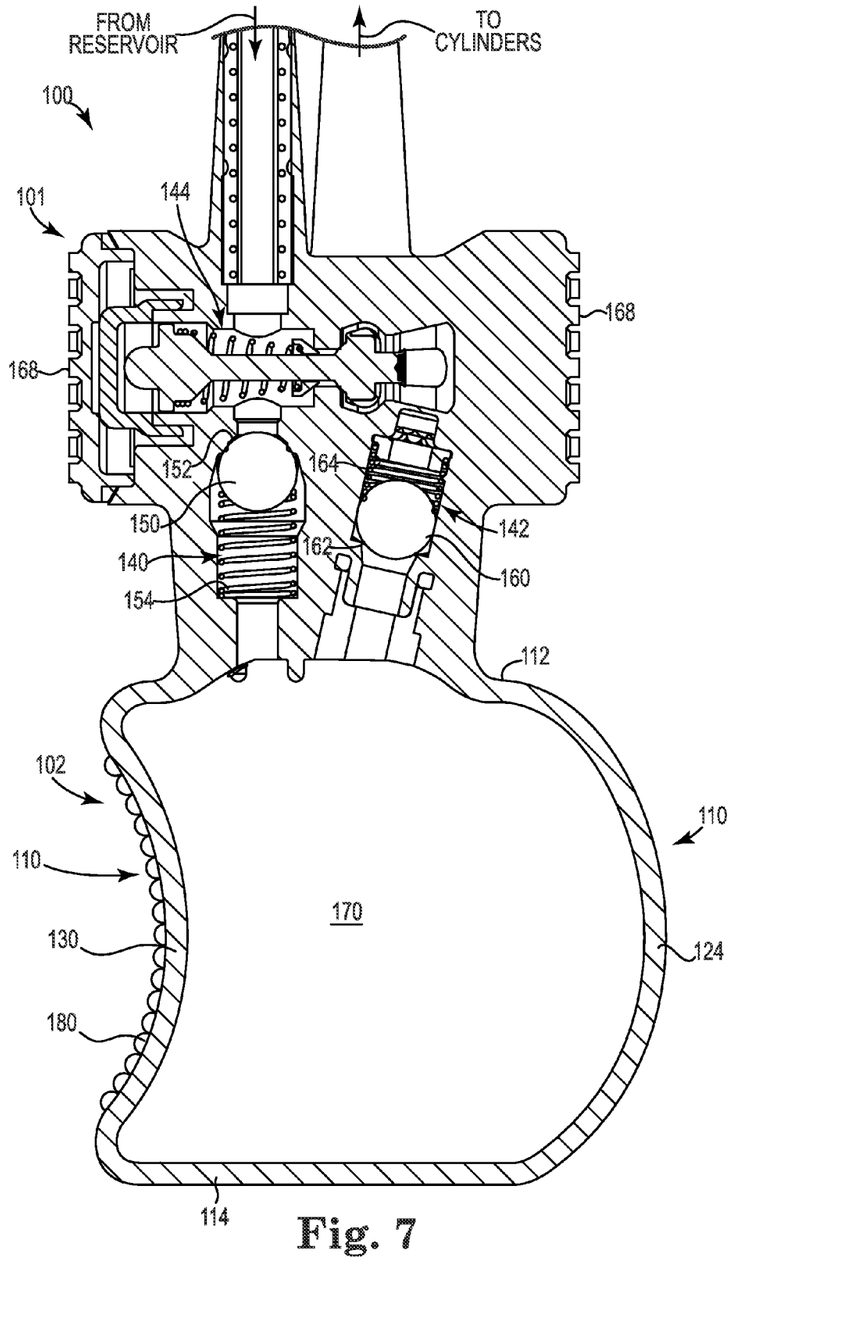
FIG. 7 is a longitudinal cross-sectional view of the pump illustrated in FIG. 6.

FIG. 7 is a longitudinal cross-sectional view of the pump 100 taken through the side wall 130 from the top surface 112 to the bottom surface 114 between the lobe 120 and the lobe 122.

The stem 101 includes an inlet valve 140 that communicates between the reservoir 22 (FIG. 1) and the pump bulb 102, an exhaust valve 142 that communicates between the pump bulb 102 and the cylinders 24, and a deflate valve 144 disposed in the stem 101 transversely between the inlet valve 140 and the exhaust valve 142.

The inlet valve 140 includes a ball 150 that is biased into contact with a surface 152 by a spring 154. The ball 150 is configured to be displaced from the surface 152 (thus compressing the spring 154) when liquid flows from the reservoir through the inlet tube 28 (FIG. 1) and into the pump bulb 102. When the liquid flow from the reservoir is reduced, or more specifically, when the pressure driving the liquid flow from the reservoir is reduced, the spring 154 biases the ball 150 into contact with the surface 152 to seat the ball 150 on the surface 152 and block backflow of the liquid from the bulb 102 back to the reservoir. In this manner, the inlet valve 140 provides a one-way inlet valve.

The exhaust valve 142 includes a ball 160 that is biased into contact with a surface 162 by a spring 164. The ball 160 is configured to be displaced from the surface 162 (thus compressing the spring 164) when liquid flows from the pump bulb 102 through the exhaust valve 142 toward the cylinders. For example, compressing the pump bulb 102 ejects liquid from the pump bulb 102, which unseats the ball 160 from the surface 162 to allow the liquid to flow past the ball 160 and the deflate valve 144 into the cylinders. Expansion (or recovery) of the pump bulb 102 draws liquid from the reservoir, past the ball 160, and into the bulb 102. The spring 164 biases the ball 160 into contact with the surface 162 to block backflow of liquid from the cylinders into the pump bulb 102. In this manner, the exhaust valve 142 provides a one-way exhaust valve.

The deflate valve 144 is configured to allow liquid to flow from the reservoir 22 into the pump bulb 102 and out the pump bulb 102 into the cylinders 24 during inflation of the cylinders (FIG. 1) as described above. The deflate valve 144 is also configured to allow for the rapid deflation of the cylinders 24. For example, in one embodiment pressing on the activation surface 168 moves the deflate valve 144 to the right in the orientation of FIG. 7, which allows fluid to flow from the cylinders 24 axially along the deflate valve 144 directly back into the reservoir 22.

The pump bulb 102 includes three lobes 120, 122, 124 that are concave relative to the internal cavity 170 and three multi-concave side walls 130, 132, 134 that are concave both when viewed in a longitudinal cross-section taken from the top surface 112 through the bottom surface 114 and concave when viewed in a lateral cross-section taken parallel between the top surface 112 and the bottom surface 114.

In one embodiment, the side surface 110 is provided with ribs 180 that increase the friction of the pump bulb 102 when grasped by the user. In one embodiment, the bottom surface 114 is convex and bulges outward relative to the internal cavity 170.

The ribs 180 can be provided with the pump 26 (FIG. 1), for example across the pump bulb 42. The convex bottom surface 114 provided on the pump 100 is also suitable for the pump 26. The attributes of the pump bulbs described in this specification are examples and are not limited to the embodiment being described. The attributes of the pump bulbs can be "mixed and matched" across the various examples, and the matrix of different pump bulb attributes described in this specification have been contemplated by the inventor. Thus, while multiple embodiments of pumps have been described the various features of the embodiments are not limited to the specific pump that is described.

Figure 8:
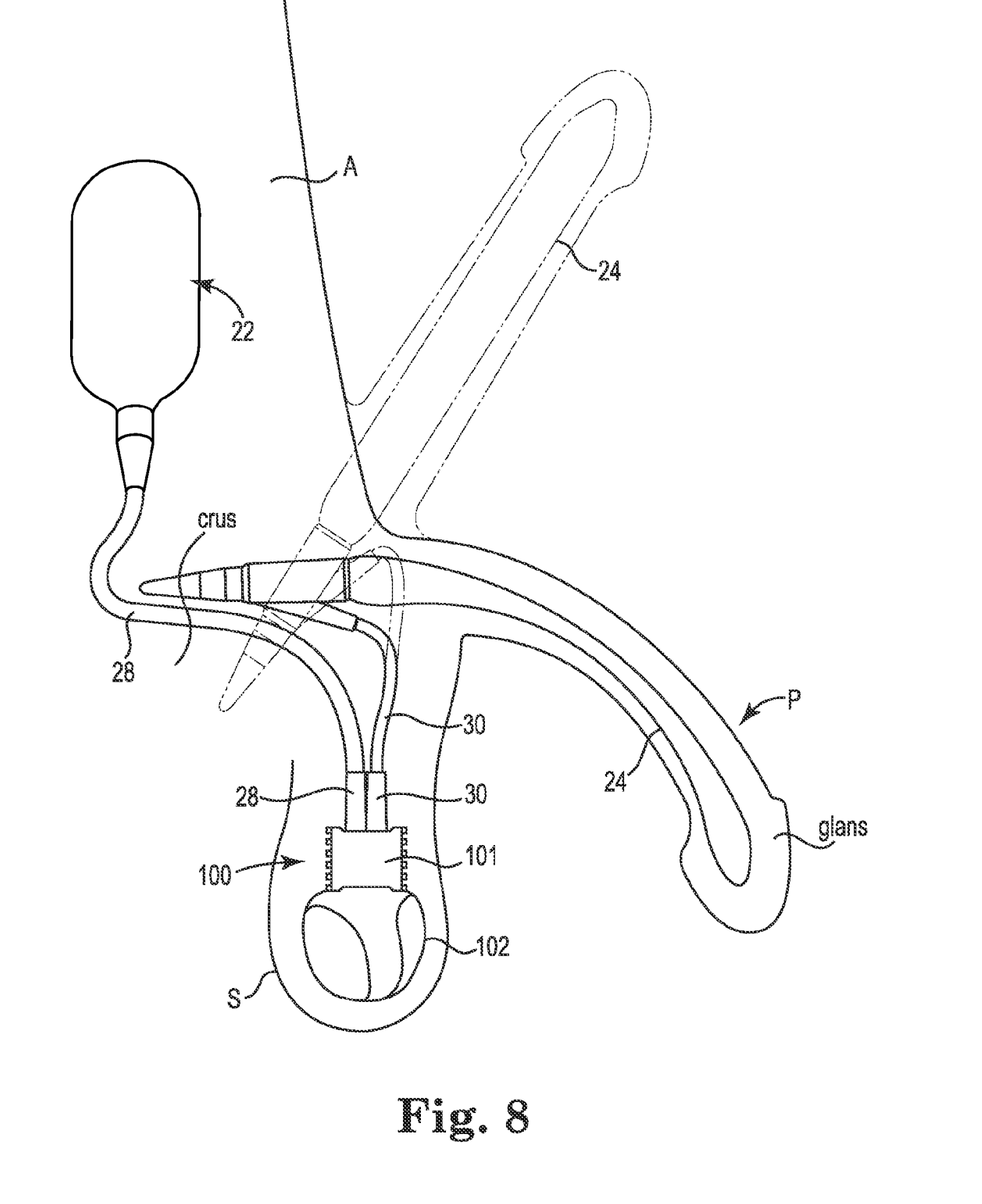
FIG. 8 is a schematic view of the implantable penile prosthetic implanted in a user.

FIG. 8 is a schematic view of the reservoir 22 implanted in an abdomen A and the pair of cylinders 24 implanted in a penis P with the pump 100 intra-operatively connected to the reservoir 22 by the tubing 28 and connected to the cylinders 24 by the tubing 30.

The reservoir 22 is suitable for implantation into the abdomen behind the abdominal fascia, or in the space of Retzius, or another suitable location determined by the surgeon. The cylinders 24 are implanted into the penis from a proximal location at the crus to a distal location at the glans.

The pump 100 is implanted in the scrotum S in a manner that allows the user to manually access both stem 101 and the pump bulb 102. The lobes 120, 122, 124 (FIG. 6) direct the user's fingers and thumb to the walls between the lobes and into a position that allows for maximum compression of the bulb 102. The concave walls 130, 132, 134 provide a spacing that allow the fingers and the thumb to compress the pump bulb 102 in the most efficient manner. The lobes in combination with the concave walls provide a pump bulb 102 that is easier to manually locate and subsequently squeeze when inflating the cylinders 24 of the penile prosthetic.

Figure 9:
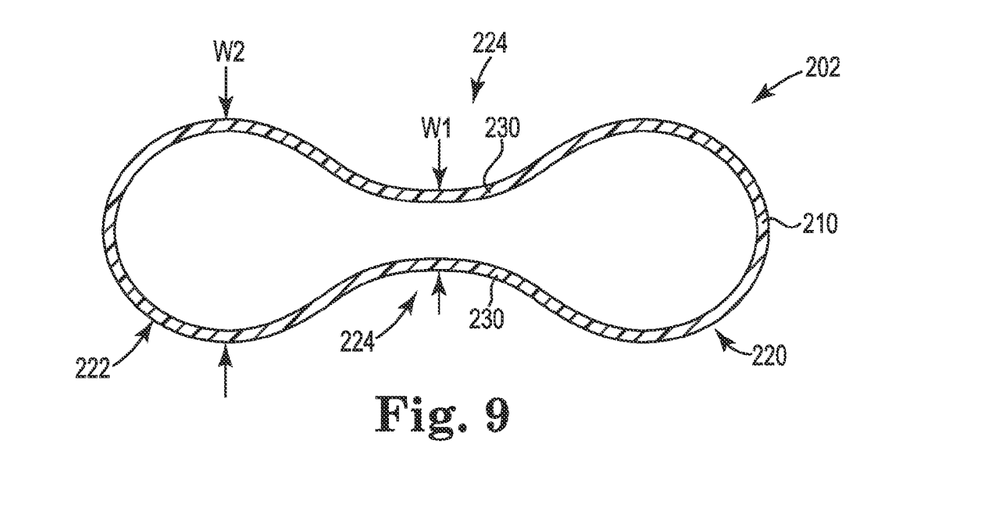
FIG. 9 is a lateral cross-sectional view taken parallel between a top surface and a bottom surface of one embodiment of a bulb of a pump.

FIG. 9 is a lateral cross-sectional view taken parallel between a top surface and a bottom surface of one embodiment of a two lobe bulb 202 suitable for use in those pumps described above.

The pump bulb 202 has an internal cavity that is formed by a side surface 210 connected between a top surface (not shown) and a bottom surface (not shown) of the bulb 202. The side surface 210 forms an outer circumference of the pump bulb 202. The pump bulb 202 includes two lobes 220, 222. Each lobe is convex in shape when viewed in a lateral cross-section taken parallel between the top surface and the bottom surface (as shown). Each lobe 220, 222 is also convex in shape when viewed in a longitudinal cross-section taken from the top surface to the bottom surface. Each lobe is spaced apart from an adjacent lobe by a spacing 224 that provides access for a finger of the user.

The side surface 210 of the pump bulb 202 provides side walls 230 that are connected between the lobes 220, 222. The side walls 230 are concave (curved inwards) when viewed in the lateral cross-section taken parallel between the top surface and the bottom surface of the pump bulb (as shown). The side walls 230 may be fabricated to be planar when viewed in a longitudinal cross-section taken from the top surface to the bottom surface between the two lobes 220, 222. Alternatively, the side walls 230 may be fabricated to be concave (curved inwards) when viewed in a longitudinal cross-section taken from the top surface to the bottom surface between the two lobes 220, 222 (e.g., See FIG. 7). Embodiments include the bulb 202 provided with at least an exterior surface of the side walls fabricated to have a plurality of friction-increasing ribs.

A first external width W1 between the two concave side walls 230 is less than a second external width W2 measured at the two convex lobes 220 or 222 as shown. The two side walls 230 are closer together than the width of either of the two lobes 220, 222.

Figure 10:
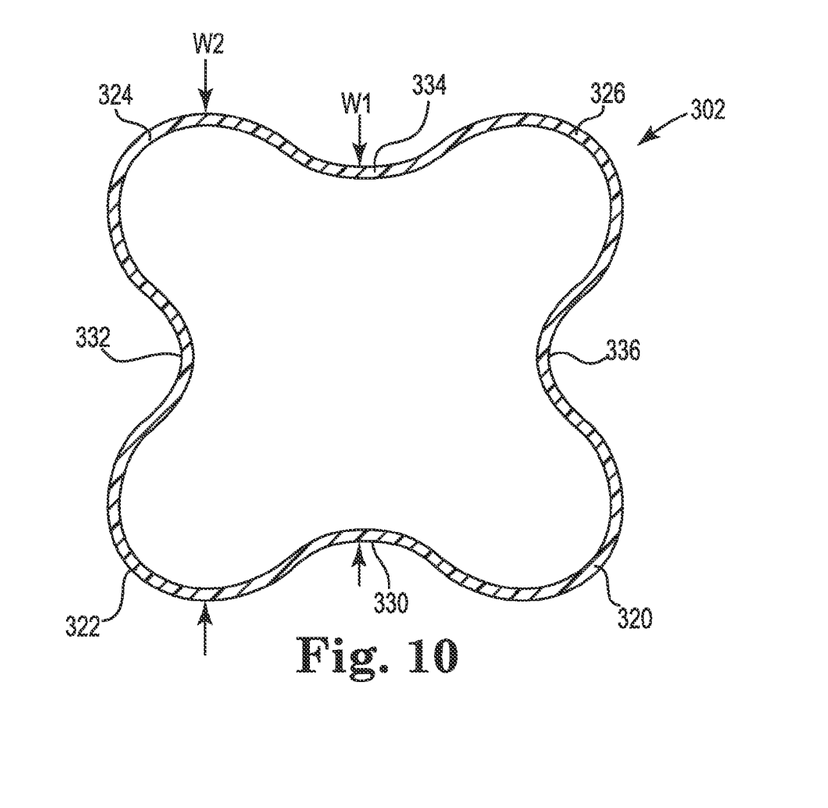
FIG. 10 is a lateral cross-sectional view taken parallel between a top surface and a bottom surface of one embodiment of a bulb of a pump.

FIG. 10 is a lateral cross-sectional view taken parallel between a top surface and a bottom surface of one embodiment of a bulb 302 suitable for use in those pumps described above. The bulb 302 has similar attributes to the bulbs 42, 102, 202 described above, but is provided in a four lobe 320, 322, 324, 326 conformation. The side walls 330, 332, 334, 336 may be fabricated to be planar or concave when viewed in a longitudinal cross-section taken from the top surface to the bottom surface between two adjacent lobes. Embodiments include the bulb 302 provided with at least an exterior surface of the side walls fabricated to have a plurality of friction-increasing ribs.

A first outside width W1 between two opposed concave side walls 330, 334 as an example is less than a second outside width W2 measured at two convex lobes 322, 324 as an example. The side walls are closer together than the width of the lobes 320, 322, 324, 326.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention be limited only by the claims and the equivalents thereof.

What is claimed is:

1. An implantable penile prosthetic comprising:
   a pump that is intraoperatively attached with tubing between an inflatable member that is implantable into a penis and a reservoir that is implantable in an abdomen, the reservoir is configured to contain liquid useful in inflating the inflatable member, the pump comprising:
   a pump bulb having an internal cavity formed by a side surface connected between a top surface and a bottom surface of the pump bulb such that the side surface forms an outer circumference of the pump bulb, and the pump bulb includes three lobes;
   wherein each of the three lobes is convex in shape when viewed in a lateral cross-section taken parallel between the top surface and the bottom surface;
   wherein each of the three lobes is spaced apart from an adjacent one of the three lobes by a spacing in a range from 0.25 to 1 inches to provide a finger-width access recess to the pump bulb; and
   wherein the side surface of the pump bulb includes three side walls, with each of the three side walls connected between two of the three lobes with each of the three side walls formed to be concave when viewed in the lateral cross-section taken parallel between the top surface and the bottom surface.

2. The implantable penile prosthetic of claim 1, wherein each of the three side walls of the pump bulb is planar when viewed in a longitudinal cross-section taken from the top surface through the bottom surface between two adjacent lobes.

3. The implantable penile prosthetic of claim 1, wherein each of the three side walls of the pump bulb is concave when viewed in a longitudinal cross-section taken from the top surface through the bottom surface between two adjacent lobes of the three lobes.

4. The implantable penile prosthetic of claim 1, wherein each of the three lobes of the pump bulb is convex in shape when viewed in a longitudinal cross-section taken from the top surface through the bottom surface.

5. The implantable penile prosthetic of claim 1, wherein the three lobes are symmetrically spaced with each of the three lobes oriented 120 degrees from an adjacent one of the three lobes.

6. The implantable penile prosthetic of claim 1, wherein the bottom surface of the pump bulb is convex and bulges outward relative to the internal cavity.

7. The implantable penile prosthetic of claim 1, wherein at least an exterior surface of the three side walls of the pump bulb includes a plurality of friction-increasing ribs.

8. The implantable penile prosthetic of claim 1, wherein the pump is sized for placement within a male scrotum.

9. The implantable penile prosthetic of claim 1, wherein the top surface of the pump bulb is intraoperatively attached to the tubing for attachment to the inflatable member that is implantable into a penis and for attachment to the reservoir that is implantable in an abdomen.

10. The implantable penile prosthetic of claim 1, the pump further comprising:
    a stem connected to the top surface of the pump bulb, the stem including an inlet valve communicating with the reservoir and an outlet valve communicating with the inflatable member.

11. The implantable penile prosthetic of claim 10, wherein the stem includes a deflation valve operable to allow the liquid in the inflatable member to flow into the reservoir and bypass the pump bulb.

12. An implantable penile prosthetic comprising:
    a pump that is intraoperatively attached with tubing between an inflatable member that is implantable into a penis and a reservoir that is implantable in an abdomen, the reservoir is configured to contain liquid useful in inflating the inflatable member, the pump comprising:
    a pump bulb having an internal cavity formed by a side surface connected between a top surface and a bottom surface of the pump bulb such that the side surface forms an outer circumference of the pump bulb, and the pump bulb includes three lobes;
    wherein each of the three lobes is convex in shape when viewed in a lateral cross-section taken parallel between the top surface and the bottom surface;
    wherein each of the three lobes is spaced apart from an adjacent one of the three lobes to provide a finger-width access recess to the pump bulb; and
    wherein the side surface of the pump bulb includes three side walls, with each of the three side walls connected between two of the three lobes with each of the three side walls formed to be concave when viewed in the lateral cross-section taken parallel between the top surface and the bottom surface.

13. A pump for an implantable penile prosthetic, the pump is intraoperatively attached with tubing between an inflatable member that is implantable into a penis and a reservoir that is implantable in an abdomen, the reservoir is configured to contain liquid useful in inflating the inflatable member, the pump comprises:
    a pump bulb having an internal cavity formed by a side surface connected between a top surface and a bottom surface of the pump bulb such that the side surface forms an outer circumference of the pump bulb, and the pump bulb includes three lobes;
    wherein each of the three lobes is convex in shape when viewed in a lateral cross-section taken parallel between the top surface and the bottom surface;
    wherein each of the three lobes is spaced apart from an adjacent one of the three lobes to provide a finger-width access recess to the pump bulb; and
wherein the side surface of the pump bulb includes three side walls, with each of the three side walls connected between two of the three lobes with each of the three side walls formed to be concave when viewed in the lateral cross-section taken parallel between the top surface and the bottom surface.

* * * * *